Figure 1:
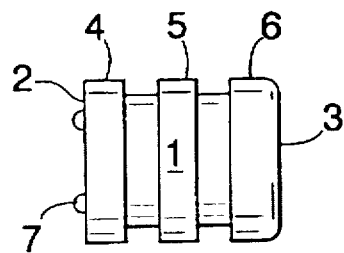

United States Patent [19]
Hjertman et al.

[11] Patent Number: 5,743,890
[45] Date of Patent: Apr. 28, 1998

[54] PISTONS FOR INJECTION CARTRIDGES

[75] Inventors: Birger Hjertman, Hässelby; Olle Ljungquist, Täby, both of Sweden

[73] Assignee: Pharmacia & Upjohn Aktiebolag, Stockholm, Sweden

[21] Appl. No.: 898,239

[22] Filed: Jul. 22, 1997

Related U.S. Application Data

[63] Continuation of Ser. No. 505,254, Oct. 12, 1995, abandoned.

[30] Foreign Application Priority Data

Feb. 17, 1993 [SE] Sweden .................. 9300525

[51] Int. Cl.$^6$ .................................................. A61M 5/315
[52] U.S. Cl. ........................................ 604/218; 604/219
[58] Field of Search .............................. 604/82, 89, 90, 604/191, 218, 219, 228, 230, 232, 221, 222; 215/50, 353, 358

[56] References Cited

U.S. PATENT DOCUMENTS

| | | | |
|---|---|---|---|
| 782,723 | 2/1905 | Campbell | 604/218 |
| 1,031,446 | 7/1912 | Hoffman | 215/358 |
| 3,939,833 | 2/1976 | Hansson et al. | 604/218 X |
| 4,492,576 | 1/1985 | Dragan | 433/90 |
| 4,723,945 | 2/1988 | Theiling | 604/232 |
| 4,781,684 | 11/1988 | Trenner | 604/110 |
| 4,929,230 | 5/1990 | Pfleger | 604/90 |
| 4,932,941 | 6/1990 | Min et al. | 604/110 |
| 5,176,639 | 1/1993 | Pozzi et al. | 604/110 |
| 5,236,420 | 8/1993 | Pfleger | 604/122 |

FOREIGN PATENT DOCUMENTS 0 111 724 A2  6/1984  European Pat. Off. .
0 160 711 A1  11/1985  European Pat. Off. .

Primary Examiner—Michael Powell Buiz
Assistant Examiner—A. T. Nguyen
Attorney, Agent, or Firm—Pollock, Vande Sande & Priddy

[57] ABSTRACT

A piston (11) to be used in displacing a liquid inside a cylindrical chamber, such as in an injection cartridge of the dual-chamber type, has at least one of its end surfaces (12) shaped convex such that said end surface or surfaces (12) are essentially planar when the piston has been arranged inside the barrel of said cartridge. Preferably both pistons in the cartridge have such a shape, their planar surfaces facing each other.

17 Claims, 2 Drawing Sheets

PISTONS FOR INJECTION CARTRIDGES

This application is a continuation of U.S. patent application Ser. No. 08/505,254, filed Oct. 12, 1995 now abandoned (the U.S. national phase of PCT Application No. PCT/SE94/00117, filed Feb. 14, 1994).

TECHNICAL FIELD

The present invention relates to improvements in pistons for displacing a liquid inside a cylindrical chamber, especially in injection cartridges. More specifically, the present invention refers to an improved shape of pistons to be used in injection cartridges, which gives an improved accuracy in the metering and dosing of preparations from said cartridges.

BACKGROUND ART

Pistons to be used in injection cartridges are usually made of rubber or a similar plastic material having resilient properties. In the manufacture of such pistons, one or both of their end surfaces are made planar and at a right angle to the longitudinal axis of the piston. Also, the planar end surfaces are often provided with a number of small projections to prevent the surfaces from sticking together in the manufacture and handling of the pistons.

When such a piston is inserted into the barrel of an injection cartridge, it will be deformed and constricted. This is because the internal diameter of the barrel must be smaller than the external diameter of the piston to assure a good seal between the piston and the internal wall of the barrel. When the piston is thus deformed elastically, its previously planar end surfaces will now assume a concave configuration, with the center of the end surface lying deeper than the peripheral portions of the surface.

The non-planar configuration of the end surface of the piston will cause a decrease in the metering accuracy when the piston is displaced by a certain distance to meter out a determined amount of a liquid preparation.

The degree of concavity is usually of the magnitude of about 0.1 mm. The displacement of the piston in the metering out of a dose of liquid is often about 1 mm. Thus, it will be seen that the concavity of the piston may cause a metering error of up to 10 percent. An error of this magnitude is usually not acceptable.

This problem is aggravated in injection cartridges of the dual-chamber type. As is known, these cartridges comprise a front chamber, which usually contains the solid component of the preparation to be injected, and a rear chamber, which usually contains the liquid component of said preparation. The two chambers are separated by a movable front piston, and the rear end of the rear chamber is sealed by a movable rear piston. When the two components are to be mixed, the rear piston is moved forward, and the pressure generated by this movement is transmitted through the essentially incompressible liquid to the front piston, which in its turn is moved forward. This forward movement of the front piston opens a bypass connection, such that the liquid in the rear chamber is made to flow over into the front chamber by the movement of the rear piston and mix with the solid component to form the desired injectable preparation. When all of the liquid component has been urged over into the front chamber, the front surface of the rear piston will abut the rear surface of the front piston, and the two pistons will now act together as one single piston in metering out the injectable preparation formed in the front chamber.

However, when the two end surfaces of the two pistons meet, they will not abut each other completely, as they are not planar. Due to the deformation, the concave surfaces formed will at first only abut each other along their peripheral portions, and this causes a spring effect, which makes the movement of the two combined pistons inaccurate. As the front piston cannot be displaced relative to the barrel without friction, and as the resting friction is greater than the friction during movement, the transmittal of the metering movement, which may be about 1 mm, will not be continuous. This means that the positioning of the front piston will not be exact, which will make the metering inaccurate.

This is especially apparent with pistons having a small mass, which are displaced with a low velocity against a considerable friction resistance. The movement of the piston rod will then not be transmitted to the front surface of the front piston without deviations.

The above spring effect will also cause the radial clamping force exerted on the barrel wall by the pistons to increase when the pistons are further deformed during the transmittal of the axial force from the piston rod. Thus, the friction force increases when the pistons are to be displaced. This makes it still more difficult to obtain the required accuracy in the metering of the injectable preparation.

Through the present invention, the problems mentioned above are largely eliminated. According to the invention, a piston of a resilient material is provided to be used in an injection cartridge of the dual-chamber type, wherein a front piston and a rear piston are arranged in a cartridge barrel, and at least one of the end surfaces of said piston has a convex shape in its unconstricted state, such that when said piston has been placed in said barrel of the cartridge, said end surface of the piston is essentially planar.

In a preferred embodiment of the invention, both the front and the rear pistons in the cartridge have at least one end surface with a convex shape, such that the two end surfaces which are to abut each other in the cartridge are essentially planar.

Figure 2:
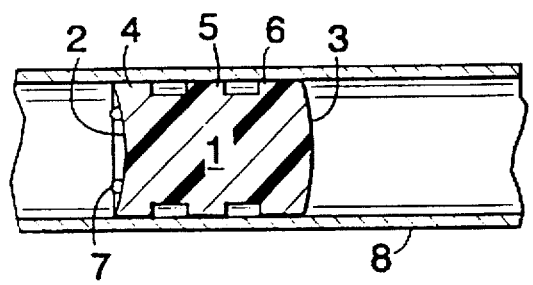
Figure 3:
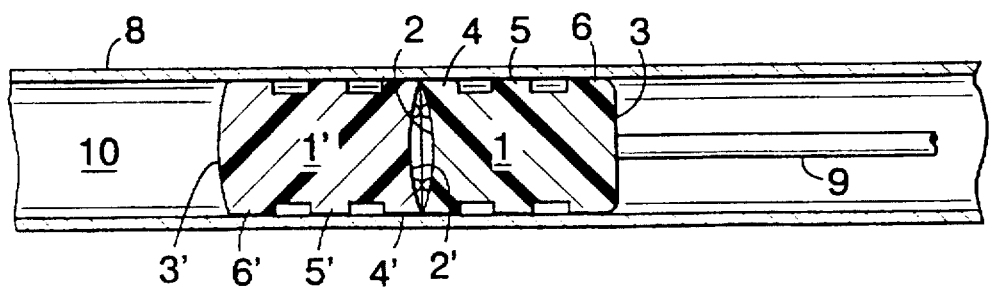
Figure 4:
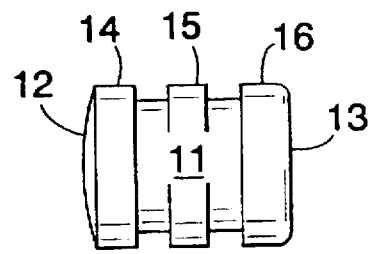
Figure 5:
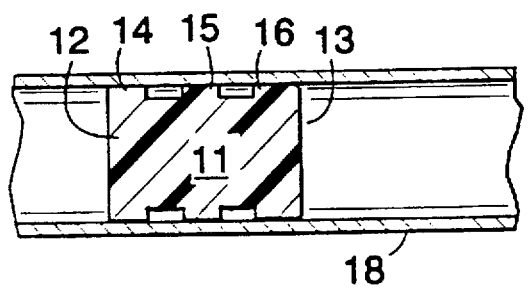
Figure 6:
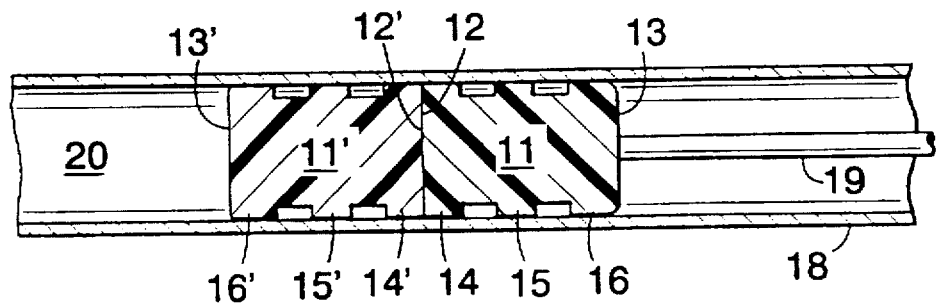

The invention is further described by means of the following specification and the appended drawings. In the drawings, FIG. 1 shows a piston according to the prior art before it has ben placed in the barrel of an injection cartridge. FIG. 2 shows the same piston after it has been arranged in said barrel. FIG. 3 shows the barrel of an injection cartridge where two pistons abut each other with their end surfaces. FIG. 4 shows a piston according to the invention before being inserted into the barrel of an injection cartridge, and FIG. 5 shows the same piston after having been inserted into said barrel. FIG. 6 shows the barrel of an injection cartridge where two pistons in accordance with the invention abut each other with their end surfaces. In the figures, like features have the same reference numbers.

FIG. 1 shows a side view of a piston of the prior art before being inserted into the barrel of an injection cartridge. The piston 1 has a front face surface 2, which is planar, and a rear face surface 3, which may be flat, convex or concave and may be provided with means (not shown) for attaching a piston rod. To achieve a better sealing effect and a decreased friction, the piston is usually provided with circumferential ridges 4, 5 and 6. Furthermore, the front planar surface of the piston may be provided with small projections 7, to prevent the planar surfaces from sticking together in the manufacture and handling of the pistons.

FIG. 2 shows a sectional view of a piston of the prior art which has been inserted into the barrel 8 of an injection cartridge. As the internal diameter of the barrel 8 is smaller than the diameter of the piston 1, the piston will be deformed inside the barrel such that the originally planar front surface 2 will be deformed into a concave shape. For reasons of clarity, the concavity of the surface 2 is shown exaggerated in the figures.

FIG. 3 shows a sectional view of a piston 1 of the prior art, which has been inserted as a rear piston into the barrel of an injection cartridge. The piston 1 has been moved forward by means of the piston rod 9 while urging the liquid phase over into a front chamber 10 through a bypass connection (not shown). When all the liquid has been urged over into the front chamber 10, the rear piston 1 will abut against a front piston 1'. This front piston 1' may have the same shape as he rear piston 1, with an originally planar rear surface 2', a front surface 3', and circumferential ridges 4', 5', and 6'. When this front piston 1' has been inserted into the barrel 8 of an injection cartridge, its rear surface 2' has been deformed from its previously planar configuration into a concave configuration, which is shown exaggerated in the figure for the sake of clarity.

It will be seen that when the front surface 2 of the rear piston 1 abuts against the rear surface 2' of the front piston 1', the two surfaces will at first only contact each other along their peripheral portions. To make the two surfaces abut each other over their complete areas, a higher force is necessary. Due to the resilience of the piston material, a spring effect is created, like that exerted by a cup spring. Because of this, a forward movement by the piston rod 9 will not be accurately transmitted to the front piston 1', and the metering of a liquid in the front chamber 10 will therefore be inaccurate. As the metering movements of the front piston may be quite small, on the order of about 1 mm or even less, it follows that inaccuracies in said movements may lead to considerable metering errors. Such errors may have serious consequences for the patient receiving the metered injection.

FIG. 4 shows a side view of a piston in accordance with the present invention. The piston 11 has a front surface 12 which has been made slightly convex. For the sake of clarity, this convexity has been exaggerated in the figure. In all other respects, the piston 11 is similar to the piston 1 shown in FIG. 1, and has a rear surface 13, which may be planar, concave or convex, and circumferential ridges 14, 15 and 16. However, no projections will be necessary on the front surface 12, as the convex surfaces will not stick together easily in the manufacture and handling of the pistons.

FIG. 5 shows a partly sectional view of a piston according to the invention having been inserted into the barrel 18 of an injection cartridge. As the internal diameter of the barrel 18 is smaller than the diameter of the piston 11, the piston will be deformed after having been placed in the barrel, and this deformation will make the originally convex front surface 12 assume a planar configuration, as is shown in the FIG. 5.

FIG. 6 shows a partly sectional view of an arrangement similar to that in FIG. 3, but using two pistons in accordance with the present invention. The rear piston 11 has been moved forward in the barrel 18 of the injection cartridge, displacing all of the liquid component through a bypass arrangement (not shown) over into the front chamber 20. The front surface 12 of the rear piston 11 now abuts the rear surface 12' of the front piston 11', and it will be seen that as the two surfaces are planar in accordance with the invention, they will contact each other over their complete surfaces, an no spring effect will arise. Therefore, a forward movement of the piston rod 19 will be accurately transmitted through the two pistons 11 and 11' into the same forward movement of the front piston 11', and the metering out of the mixed preparation in the front chamber 20 will be accurate even for very small movements.

In a preferred embodiment of the invention, the rear surface of the pistons is markedly convex or even more or less pointed, such that it clearly differs from the slightly convex front surface of the pistons. Because of the marked difference between the two surfaces, it will be easy to orient the pistons correctly by means of mechanical handling equipment when inserting them into the barrel of an injection cartridge. At the same time, no projections will be necessary on the front surfaces of the pistons, as has been stated in the foregoing. These projections contribute to the metering error, but have been considered to be necessary to prevent the pistons from sticking together with their planar surfaces. As the front surfaces are (no not longer) planar when outside of the barrel, there will be much less risk of the pistons sticking together, and the projections can thus be dispensed with.

The injection cartridge as such is of a conventional design and comprises such features as a bypass arrangement, for example a channel in the wall of the barrel, and a closure at the front end of the cartridge, which can be pierced by a hollow needle. For reasons of clarity, and as such features are well-known to those skilled in the art, these features are not shown in the figures of the drawing.

When the injection cartridge is to be used for the metering out and administering of the mixed preparation in the front chamber, it is usually placed in a holder device, which may include a metering and dosing arrangement. Many such devices are well-known to those skilled in the art, and cartridges including the piston or pistons of the present invention may be used in them without any adjustment of their function having to be made. This is a further advantage of the present invention.

The pistons of the invention may be manufactured from conventional materials which are commonly used for pistons in injection cartridges, and no special materials are necessary. Thus, the person skilled in the art may select a suitably resilient rubber or plastic material among those known for this purpose.

The degree of convexity to be given to the surface or surfaces of the pistons of the invention may be determined in a number of ways, which are apparent to those skilled in the art. The method most close at hand is by experimentation. It is easy to prepare a number of pistons having a varying degree of convexity of the end surfaces and subsequently test the pistons by inserting them in a tube having the same interior diameter as the barrel of the injections cartridge. The test piston whose end surface becomes planar inside the tube is then selected.

Another way of determining the desired convexity is by calculation. In such a calculation, one starts from the piston in its place in the cylindrical barrel and having a planar front surface. With knowledge of such parameters as the dimensions and shape of the piston and the barrel, and the elastic properties of the material used for the piston, one can calculate backwards to find the desired convexity of the piston before it is inserted into the barrel. There are computer programs available for this, using the so-called finite element method (FEM).

It is important that the internal diameter of the barrel of the injection cartridge is manufactured with a high precision and accuracy. Small deviations in the internal diameter have a profound influence on the shape of the front surface of the piston when it has been inserted into the barrel, and thus also on the metering accuracy.

Except for the convex shape of one or both end surfaces, the shape of the pistons of the invention is the same as that of conventional pistons for use in injection cartridges. This gives the advantage that the mold used for the manufacture of the pistons will only have to be slightly modified. Also the process for the manufacture of the pistons will be essentially unchanged from the conventional process. As the convex surfaces of the pistons will not have the same tendency as the conventional flat surfaces to stick together during the manufacture and handling of the pistons, there will be no need to provide the surfaces with small projections.

When necessary, the pistons of the invention are provided with a suitable attachment for a piston rod. This attachment may be of any conventional type.

Through the present invention, pistons for use in injection cartridges are provided which have a number of advantages in comparison to conventional pistons for the same use. As the contact surface is planar when the front and the rear pistons abut each other in an injection cartridge, the "spring effect" is eliminated. This leads to an improved accuracy in the metering of the preparation which is to be administered. Furthermore, the force necessary to displace the two pistons together is decreased, which leads to less stringent requirements of an antifriction treatment of the intrior wall of the cartridge or the surface of the piston, such as siliconizing.

In the foregoing specification, the invention has been described and exemplified with special reference to the drawing. However, it goes without saying that other embodiments and variants of the invention are possible without going outside the scope of the appended claims. Thus, although the advantages of the invention are most apparent in the metering of liquid doses froma dual-chamber injection cartridge, the invention also brings advantages when used in simple injection syringes and single-chamber cartridges. In general, the invention can be applied whenever a liquid is to be precision metered into doses by the displacement of a piston inside a cylindrical or tubular chamber.

We claim:

1. In a liquid displacement arrangement comprising a barrel having at least a section which has an essentially cylindrical shape and at least one piston of resilient material wherein said at least one piston has:
   a) a substantially cylindrical mantle surface or circumferential ridges, and
   b) at least one end surface substantially transversal to the cylindrical mantle surface or circumferential ridges, and the barrel surrounding the piston having a barrel interior surface in contact with the mantle surface or circumferential ridges,
   the improvement comprising that the piston end surface is deformation corrected,
   i) in that said end surface has a convex shape under unstressed conditions for the piston resilient material, and
   ii) in that the degree of end surface convexity under unstressed conditions is adapted to give an essentially planar end surface shape under conditions of mantle surface constriction or circumferential ridges constriction, and that the barrel internal diameter and the piston external diameter are adapted to provide said conditions of constriction.

2. The arrangement of claim 1, wherein said barrel comprises an outlet and said deformation corrected piston end surface faces said outlet.

3. The arrangement of claim 1, wherein a second piston, which has at least one deformation corrected end surface, is arranged within said barrel under said conditions of constriction, the deformation corrected surfaces of the pistons facing each other and being essentially planar.

4. The arrangement of claim 3, wherein said barrel comprises an outlet and at least the piston closest to said outlet has a second deformation corrected surface facing the outlet.

5. The arrangement of claim 4, wherein the barrel comprises a bypass arrangement for liquid transfer past one of the pistons.

6. The arrangement of claim 1, wherein said resilient material is selected from the group consisting of resilient rubbers and resilient plastics.

7. An injection cartridge of the dual-chamber type, comprising a front piston and a rear piston arranged inside a barrel, said barrel having at least a section which has an essentially cylindrical shape and at least one of said front piston and said rear piston being of resilient material wherein said at least one of said front piston and said rear piston has:
   a) a substantially cylindrical mantle surface or circumferential ridges, and
   b) at least one end surface substantially transversal to the cylindrical mantle surface or circumferential ridges, and the barrel surrounding the piston having a barrel interior surface in contact with the piston mantle surface or circumferential ridges,
   the improvement comprising that the piston end surface is deformation corrected,
   i) in that said end surface has a convex shape under unstressed conditions for the piston resilient material, and
   ii) in that the degree of end surface convexity under unstressed conditions is adapted to give an essentially planar end surface shape under conditions of mantle surface constriction or circumferential ridges constriction, and that the barrel internal diameter and the piston external diameter are adapted to provide said conditions of constriction.

8. The injection cartridge of claim 7, wherein said barrel comprises an outlet and said deformation corrected piston end surface faces said outlet.

9. The injection cartridge of claim 7, wherein the other of said at least one of said front piston and said rear piston, which has at least one deformation corrected end surface, is arranged within said barrel under said conditions of mantle surface constriction, the deformation corrected surfaces of the front and rear pistons facing each other and being essentially planar.

10. The injection cartridge of claim 9, wherein said barrel comprises an outlet and at least the front piston has a second deformation corrected surface facing the outlet.

11. The injection cartridge of claim 10, wherein the barrel comprises a bypass arrangement for liquid transfer past one of the pistons.

12. The injection cartridge of claim 7, wherein said resilient material is selected from the group consisting of resilient rubbers and resilient plastics.

13. In a piston of a resilient material, for use in displacing a liquid inside a cylindrical chamber wherein, the piston has an external diameter adapted for causing mantel surface constriction when placed inside said cylindrical chamber and having:
   a) a substantially cylindrical mantle surface or circumferential ridges, and
   b) at least one end surface which is substantially transversal to the cylindrical mantle surface or circumferential ridges, the improvement comprising that the piston end surface is deformation corrected, i) in that said end surface has a convex shape under unstressed conditions for the piston resilient material; and ii) in that the degree of end surface convexity under unstressed conditions is adapted to give an essentially planar end surface shape under conditions of mantle surface or circumferential ridges constriction.

14. The piston of claim 13, wherein said resilient material is selected from the group consisting of resilient rubbers and resilient plastics.

15. The piston of claim 13, comprising two deformation corrected end surfaces.

16. The piston of claim 13, comprising a second end surface having a shape which is one of flat, convex or concave.

17. The piston of claim 13, comprising a second end surface which is provided with means for attaching a piston rod.

* * * * *